US00PP31169P2

(12) United States Plant Patent
Hansen

(10) Patent No.: US PP31,169 P2
(45) Date of Patent: Dec. 3, 2019

(54) ***PHLOX* PLANT NAMED 'EYE SHADOW'**

(50) Latin Name: *Phlox subulata*
Varietal Denomination: Eye Shadow

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,914

(22) Filed: Feb. 1, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ..... A01H 5/02; A01H 6/70
See application file for complete search history.

*Primary Examiner* — Annette H Para

(57) ABSTRACT

A unique cultivar of Hybrid Spring *Phlox* named *Phlox* 'Eye Shadow' characterized by vigorous, multi-stemmed, spreading, winter-hardy habit with short, bright glossy-green, awl-shaped leaves. Flowering begins in mid-April and continuing for nearly five weeks on heavily-branched peduncles and completely cover the plant in peak season. Petals are vibrant, rosy-purple with a large eye of striae marks of dark wine purple. Petal apices are moderately notched. Foliage stays clean and resists mildew, and the new plant is especially suitable for the landscape as a potted plant and in the garden as a specimen or en masse.

1 Drawing Sheet

Botanical classification: *Phlox subulata.*
Variety denomination: 'Eye Shadow'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Phlox* 'Eye Shadow' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Eye Shadow' and will be referred to hereafter by its cultivar name, 'Eye Shadow', or the "new plant". The new plant was hybridized by the inventor at a wholesale perennial nursery in Zeeland, Mich. on May 1, 2013 as cross between *Phlox subulata* 'Purple Beauty' (not patented) as the female parent times *Phlox subulata* 'North Hills' (not patented) as the male parent. The new plant was passed initial evaluation on the spring of 2015 and was assigned the breeder code 13-83-1 through the remaining evaluation process. 'Eye Shadow' was first asexually propagated by stem cuttings in the greenhouses at the same nursery in Zeeland, Mich. in the summer of 2015. The unique characteristics of the new plant have been found to be reproducible and stable in successive generations of asexually propagated and the resultant plants have been found to be identical to the original selection.

BRIEF SUMMARY OF THE PLANT

*Phlox* 'Eye Shadow' is unique from all other Creeping *Phlox* known to the inventor. The nearest comparison plants known to the inventor include: 'Blue Emerald' (not patented), 'Red Wing' (not patented) and the copending cultivar 'Eye Candy' Plant patent application Ser. No. 16/350,912. 'Blue Emerald' has flowers of a delicate lavender-blue. 'Red Wing' has flowers of bright crimson-pink. The female parent, 'Purple Beauty' has flowers that are bright purple with a deep violet eye and deeper cleft petal apices. The male parent, 'North Hills' has flowers that are bright white with prominent violet purple eye and is slightly more vigorous with repeat flowering. 'Eye Candy' has flowers that are light lavender-pink and less deeply cleft petal lobe apices.

*Phlox* 'Eye Shadow' differs from and all other *Phlox* known to the inventor in the following repeatedly observed traits in combination:

1. Vigorous plants of compact mounded habit, spreading by rooting stems, producing short, clean, glossy, bright-green, awl-shaped leaves;
2. Multiple heavily-branched stems produce branched panicles;
3. Flower beginning in mid-April and continuing for nearly five weeks completely covering plant at peak flowering;
4. Flowers of vibrant, rosy-purple with prominent dark-purple eye;

BRIEF DESCRIPTION OF THE DRAWINGS

The photographs of the new plant demonstrate the unique traits of *Phlox* 'Eye Shadow' and the overall appearance of the plant at two-years-old growing in a full-sun production field in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
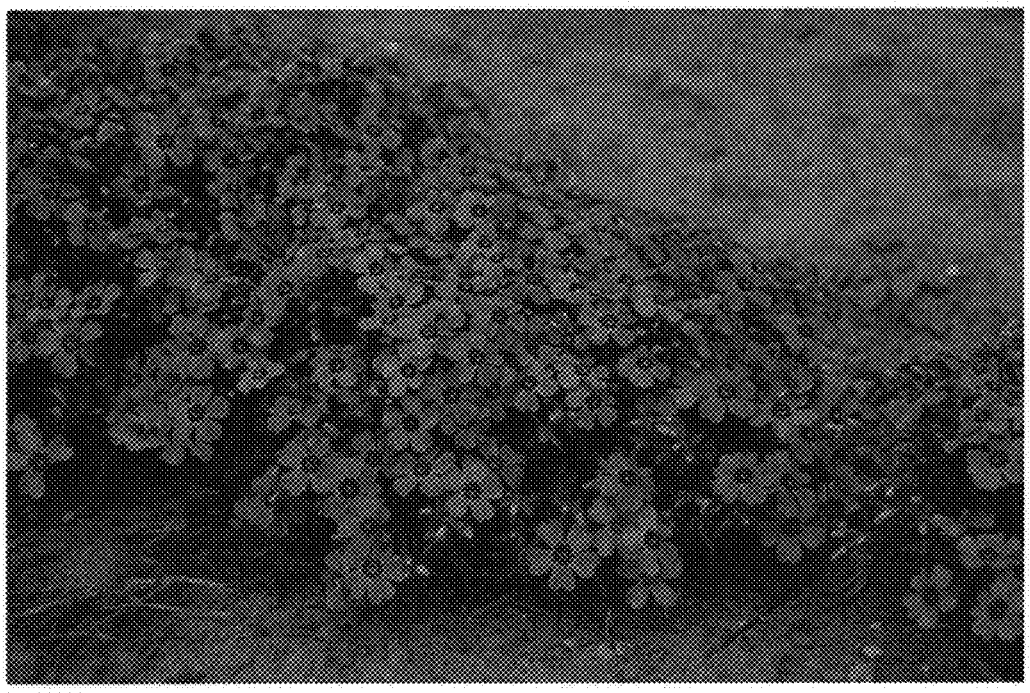
FIG. 1 shows the new plant in peak flower.
Figure 2:
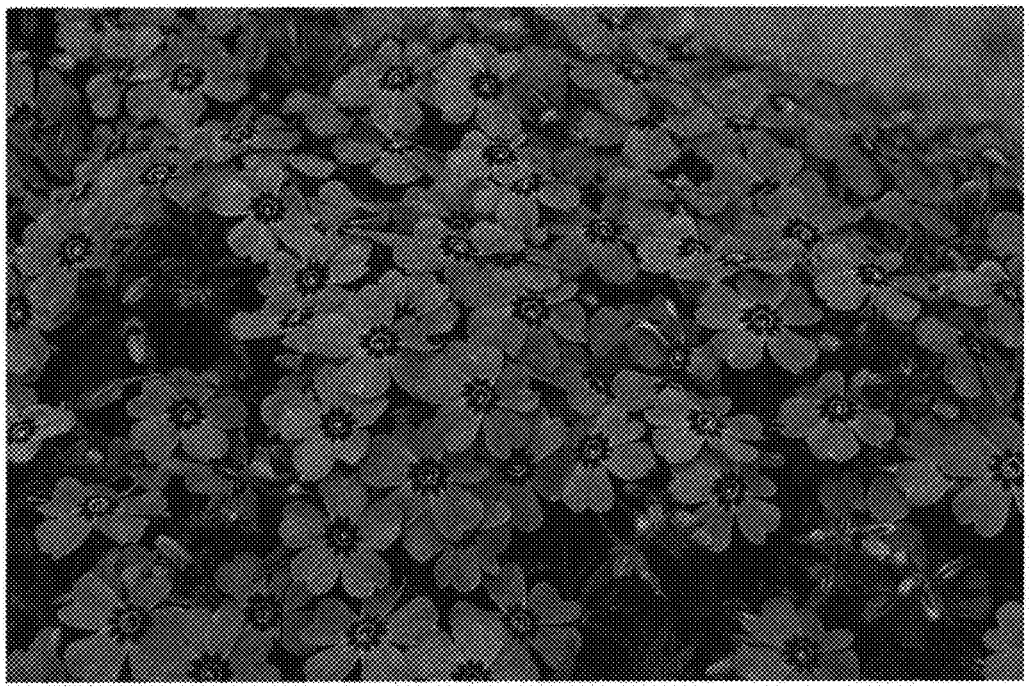
FIG. 2 shows a close-up of the flowers and buds.

The following descriptions and color references are based on the 2015 edition of The Royal Horticultural Society Colour Chart except where common dictionary terms are used. *Phlox* 'Eye Shadow' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox subulata;*

Parentage: Female or seed parent is *Phlox subulata* 'Purple Beauty', male or pollen parent is *Phlox subulata* 'North Hills';

Plant habit: Winter-hardy, evergreen herbaceous perennial; compact, highly branched; producing about 50 to 75 stiff, highly-branched stems; foliage 15.0 cm tall and 80.0 cm wide, average 14.5 cm tall and 71.0 cm wide; flowering to 18.0 cm tall and 84.0 cm wide;

Propagation: Stem cuttings; rooting in about 3 weeks;

Time to produce finished crop in 3.8 liter pots: About 6 to 9 weeks; vigorous;

Root: Fibrous and freely branching; color creamy white to tan depending on soil type;

Leaves: Simple; opposite proximally, whorled distally; linear to subulate; apex apiculate; base truncate, clasping; margin entire, micro-ciliolate; lustrous and glabrous both adaxial and abaxial; about 13.0 mm long by about 3.0 mm wide, average about 10.0 mm long and 1.5 mm wide;

Leaf color: Adaxial expanding and mature nearest RHS 138A; abaxial expanding and mature nearest RHS 146B;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; to 1.5 mm diameter near base and branching with two branches at nearly every distal node; internodes about 1.9 mm long distally; upright to outright; covered in leaves distally; about 11.5 cm long and 1.5 mm diameter at base;

Stem color: Nearest RHS 146D proximally, covered in leaves distally;

Nodes: Proximally about 5.0 mm apart; distally less than 1.0 mm apart;

Node color: Same as surrounding stem;

Flowers: Perfect; salverform; slightly reflexed; about 16.0 mm across the flat face and 14.0 mm long; with fused corolla tube about 13.0 mm long and 2.0 mm diameter near face; in branched panicle of about 4 to 8 flowers; attitude upright to outwardly;

Flower longevity: About 5 days on plant; self-cleaning;

Flower fragrance: Faintly sweet;

Buds one to two days prior to opening: Narrowly oblanceolate, to narrowly clavate; acute apex with petals implicate; about 13.0 mm long, 5.0 mm long in terminal bulb portion and 8.0 mm long in tube; tube to 2.0 mm diameter;

Bud color: Nearest RHS N75D in distal bulb portion, exposed tube nearest RHS 84A, 1.0 mm wide ring between bulb and tube nearest RHS 79A;

Petals: Five; cleft blade and claw base fused into tube; apex emarginate less than 2.0 mm deep; blades slightly imbricate; glabrous adaxial and abaxial except adaxial surface 3.0 mm basal portion;

Petal size: Blade about 8.0 mm long and 8.0 mm wide near center; tube about 13.0 mm long and 2.0 mm diameter;

Petal color:

Young adaxial: Center and distal blade between RHS N78B and RHS NN78D, with 2.0 mm center eye nearest RHS N79A; basal 2.0 mm of tube nearest RHS 145D, remaining portion nearest RHS 76D;

Young abaxial: Basal 2.0 mm of tube nearest RHS 145D, distal half of tube nearest RHS N77D and middle portion nearest RHS 76D; blade nearest RHS 76A micro-punctate with dots nearest RHS N74D;

Mature adaxial: Center and distal blade between RHS N78C and NN78D, with 2.0 mm center eye nearest RHS N79A; basal 2.0 mm of tube nearest RHS 145D, remaining portion nearest RHS 76D;

Mature abaxial: Basal 2.0 mm of tube nearest RHS145C, distal half of tube nearest RHS N77D and middle portion nearest RHS 76D, blade between RHS 76A and RHS 76B;

Androecium: Typically five;

Filaments: Typically five, adnate to inner corolla at various heights about 10.0 mm to 12.0 mm from base; about 1.0 mm long and 0.1 mm in diameter; color nearest RHS NN155D;

Anther: Five; oblong elliptic; dorsifixed; oblong, about 2.0 mm long by 1.0 mm wide; color nearest RHS 15A;

Pollen: Nearly microscopic, spherical; color nearest RHS 23A;

Gynoecium: One pistil per flower; 14.0 mm long;

Style: Cylindrical; about 11.5 mm long and 0.2 mm diameter when flower is mature; persistent after flower abscission; color nearest RHS 155A;

Stigma: Trifid in proximal 1.0 mm long, about 0.2 mm diameter; color between RHS 157A and RHS 158A;

Ovary: Inferior; globose, rounded to slightly obtuse apex and truncate base; about 1.5 mm long and 1.0 mm diameter; color nearest RHS 143A;

Calyx: Campanulate; pubescent abaxial, glabrous adaxial; about 7.0 mm long and 4.5 mm across at apex;

Sepals: Five; lanceolate; glabrous adaxial and puberulent abaxial; narrowly acute apex, fused in basal 3.0 mm; margin entire; pubescent abaxial, glabrous and lustrous adaxial; individually about 7.0 mm long and 1.0 mm wide at fusion;

Sepal color: Adaxial nearest RHS 138A, abaxial nearest RHS 138A with light blush of nearest RHS 187A;

Peduncle: Finely puberulent; strong, flexible; upright to outwardly, cylindrical; about 2.8 mm diameter at base and 1.0 cm long;

Peduncle color: Nearest RHS 146D lightly tinted with RHS 183B;

Pedicle: Cylindrical; finely puberulent; flexible; upright to outwardly; size variable, 6.0 mm to about 13.0 mm long and 0.7 mm diameter;

Pedicle color: Nearest RHS 183B;

Fruit: Globose; lustrous; 2.0 mm diameter and 2.5 mm tall; color nearest RHS 199C;

Seeds: Typically one per flower; elliptical; rounded apex and base; about 2.0 mm tall and 1.5 mm across middle; color nearest RHS 200A;

Hardiness and culture: The new plant grows best with plenty of moisture and adequate drainage; hardy to at least from USDA zone 2 through 9.

Disease and pest resistance: *Phlox* 'Eye Shadow' demonstrates excellent powdery mildew resistance under conditions that would normally show symptoms.

I claim:

1. A new and distinct cultivar of *Phlox* plant named 'Eye Shadow' as herein described and illustrated.

* * * * *